United States Patent
Garcia

(10) Patent No.: US 12,082,833 B2
(45) Date of Patent: Sep. 10, 2024

(54) SURGICAL INSTRUMENT

(71) Applicant: Annalyn Garcia, Lummen (BE)

(72) Inventor: Annalyn Garcia, Lummen (BE)

( * ) Notice: Subject to any disclaimer, the term of this patent is extended or adjusted under 35 U.S.C. 154(b) by 206 days.

(21) Appl. No.: 17/416,233

(22) PCT Filed: Dec. 23, 2019

(86) PCT No.: PCT/EP2019/086938
§ 371 (c)(1),
(2) Date: Jun. 18, 2021

(87) PCT Pub. No.: WO2020/128094
PCT Pub. Date: Jun. 25, 2020

(65) Prior Publication Data
US 2022/0071648 A1    Mar. 10, 2022

(30) Foreign Application Priority Data
Dec. 21, 2018  (BE) .................................. 2018/5935

(51) Int. Cl.
*A61B 17/28*    (2006.01)

(52) U.S. Cl.
CPC ........ *A61B 17/282* (2013.01); *A61B 17/2833* (2013.01); *A61B 17/2841* (2013.01)

(58) Field of Classification Search
CPC ..... A61B 17/04; A61B 17/0483; A61B 17/12; A61B 17/28; A61B 17/282; A61B 17/2812; A61B 17/2833; A61B 17/2841; A61B 17/30; A61B 17/3201; A61B 2017/2926; A61B 2017/2945; A61B 17/29; B25B 7/00; B25B 7/02

USPC .......................................... 606/207; 433/159
See application file for complete search history.

(56) References Cited

U.S. PATENT DOCUMENTS

| | | | | |
|---|---|---|---|---|
| 1,510,416 | A | * 9/1924 | Pietz ................... | A61B 17/2812 606/208 |
| 2,944,341 | A | * 7/1960 | Lane ........................ | A61C 3/14 D24/153 |
| 3,503,398 | A | 3/1970 | Fogarty et al. | |
| 3,646,939 | A | * 3/1972 | Sklar .................... | A61B 17/282 606/207 |
| 3,762,417 | A | * 10/1973 | Textor ................ | A61B 17/2812 606/135 |

(Continued)

FOREIGN PATENT DOCUMENTS

| CN | 204520873 U | 8/2015 |
|---|---|---|
| CN | 107773287 A | 3/2018 |

(Continued)

OTHER PUBLICATIONS

International Preliminary Report mailed Nov. 27, 2020 in reference to co-pending European Patent Application No. PCT/EP2019/086938 filed Dec. 23, 2019.

(Continued)

*Primary Examiner* — Sarah W Aleman
(74) *Attorney, Agent, or Firm* — Dinsmore & Shohl LLP

(57) ABSTRACT

A surgical forceps is provided that is configured for treating and/or cutting tissue. The surgical forceps is based on the so named 'mosquito forceps' and provides a clamping configuration of the tip that is particularly useful for neuropathic skin surgery, such as in case of diabetes or other skin irregularities e.g. the callus or the like.

13 Claims, 3 Drawing Sheets

(56) References Cited

U.S. PATENT DOCUMENTS

| | | | | |
|---|---|---|---|---|
| 5,275,615 | A | * | 1/1994 | Rose .................. A61B 17/29 606/208 |
| 5,618,305 | A | * | 4/1997 | Lolagne .................. A61F 6/204 606/205 |
| 5,624,454 | A | | 4/1997 | Palti et al. |
| 5,674,244 | A | * | 10/1997 | Mathys .............. A61B 17/2833 606/208 |
| 5,797,919 | A | * | 8/1998 | Brinson ............. A61B 17/8866 606/205 |
| 7,128,575 | B1 | * | 10/2006 | Sohn ..................... A61C 3/14 81/418 |
| 7,264,623 | B2 | * | 9/2007 | Harris, Jr. ............. A61B 17/29 606/148 |
| D625,008 | S | * | 10/2010 | Boedeker ..................... D24/143 |
| 2003/0004523 | A1 | * | 1/2003 | Chan .................... A61B 17/062 606/148 |
| 2008/0300622 | A1 | | 12/2008 | Xu |
| 2010/0241128 | A1 | * | 9/2010 | Falahee .............. A61B 17/7074 606/90 |
| 2018/0078271 | A1 | | 3/2018 | Thrasher, III |

FOREIGN PATENT DOCUMENTS

| | | |
|---|---|---|
| DE | 1060546 B | 7/1959 |
| EP | 0256966 A2 | 2/1988 |
| GB | 2227200 A | 7/1990 |

OTHER PUBLICATIONS

International Search Report mailed Mar. 13, 2020 in reference to co-pending European Patent Application No. PCT/EP2019/086938 filed Dec. 23, 2019.

* cited by examiner

SURGICAL INSTRUMENT

CROSS REFERENCES TO RELATED APPLICATIONS

This application is a national-stage application under 35 U.S.C. § 371 of International Application No. PCT/EP2019/086938, filed Dec. 23, 2019, which International Applications claims benefit of priority to Belgian Patent Application No. 2018/5935, filed Dec. 21, 2018.

FIELD OF THE INVENTION

The present disclosure relates to surgical instruments and, more particularly, to a surgical forceps configured for treating and/or cutting tissue. The surgical forceps of the present invention is based on the so named 'mosquito forceps' and provides a new clamping configuration of the tip making it particularly useful for neuropathic skin surgery, such as in case of diabetes or other skin irregularities e.g. the callus or the like.

BACKGROUND TO THE INVENTION

A surgical forceps is a plier-like device which relies on mechanical action between its jaws to grasp, clamp, and constrict tissue. Such surgical forceps are conventionally used as a removal tool wherein the therapist uses the forceps to grab, lock and manipulate the neuropathic skin at the position of the irregularity or disease, and treat, remove or cut it away by means of another specific tooling, e.g., a scalpel, without affecting or damaging the healthy skin sections. The forceps is handled by the therapist with one hand, whilst the other treatment tooling is manipulated by the other hand.

In the context of the treatment of neuropathic skin it is of highly importance to: i) have a sufficiently large grip level or total clamping force; ii) being able to grab a relatively large section or bulb of the neuropathic skin and have an equal force distribution over the grabbed skin section; iii) experience a high level of stability of the clamping forceps as such that the treatment tooling can be handled with high precision.

For this treatment mosquito forceps are currently being used. Such mosquito forceps have small, sharp ended jaws which are either straight or curved and have a locking grip with 3-5 teeth to allow ratchet clamping at various pressures. Mosquitos are normally used to retract in small fields, hold delicate tissue, and compress bleeding vessels, among other things. When used however for the treatment (removal) of skin neuropathies, they fail to meet the aforementioned requirements. In these conventional mosquito forceps, the grabbing functionality is sharp and pointy and predominantly located at the tip of its jawing head. As a consequence, only a tiny section of the neuropathic skin can be grabbed and pinched. The total clamping force is limited and the risk to lose the grip is increased significantly. The total grabbing force is exerted in one point mainly and not distributed over a whole area, which increases the risk to cause unwanted additional damage to the healthy skin significantly. Moreover, due to the fact that the forceps' clamping functionality is pointy and only located at its tip, it is able to move with a too high level of degree of freedom. As such a poor stability is experienced. As a consequence, the handling control of the other treatment tooling is poor, and the treatment is affected negatively.

Depending on the application chirurgical handling forceps will have different jaws. This is for example apparent from the atraumatic hemostatic clamp described in US patent application US2008/0300622, wherein the jaws are specifically designed to provide a reliable grasp without causing trauma to bodily vessels. As such, this chirurgical handling forceps is not suitable for treatment of skin neuropathies, requiring a firm grip over an extended skin surface. The same holds true for the forceps described in Chinese patent application CN204520873, and specifically designed as a percutaneous trachea puncture distraction forceps for maintaining the trachea open with a controlled maximum by means of the restriction body (40) present between the handles. As such, this forceps has a completely different functionality and is accordingly not suitable as a grasping tool in the treatment of skin neuropathies. Not so for the handling forceps described in US patent application US2018/078271 which is indeed designed as a grasping tool, but simply comprising a plurality pincers for holding multiple objects, even including an optional offset (50A, 50B) to adjust the space between the pincers but again not suitable as a grasping tool in the treatment of skin neuropathies requiring a firm grip over an extended skin surface.

There is accordingly a desire in the field for a forceps addressing these problems and making it suitable for neuropathic skin surgery, such as in case of diabetes or other skin irregularities e.g. the callus or the like. In the latter, and in particular in the case of wound treatment a proper tool for debridement is currently missing. Debridement is the foundation of proper wound management, and requires decallusing, picking and excision purposes. It is an object of the present invention to provide such tool, that aids in removal of dead, damaged, or infected tissue in skin neuropathies to improve the healing potential of the remaining healthy tissue, avoiding accidental or unneeded incisions of healthy tissue around the affected skin.

SUMMARY OF THE INVENTION

In providing a solution to the present problems associated with debridement of skin neuropathies the forceps according to the invention adds the decallusing functionality to existing tools like the mosquito forceps which is currently being used. Incorporating an opening in the bending section of the closed jawing head, it enables enclosing a gulp of neuropathic skin greatly enhancing the process of decallusing. In a particular embodiment the tips (7) of the jaws are as sharp as in mosquito forceps. With these sharp tips, dirt or isolated dead tissue particles can be picked from the wound area. In an even further embodiment the jaw head further includes a cutting area (9), preferably with straight cutting edges (10) similar to a nail clipper, to cut loosened materials from the affected skin.

The forceps according to the invention could accordingly be summarized in the following numbered embodiments;
1. A surgical forceps configured for neuropathic skin surgery comprising a pair of handling rings (1) at one end of a pair of handle shanks (2) pivotably connected by means of a pivotal connection (4) to a pair of jaws making up a jawing head (6) ending in a bent tip (7) and characterized in that the jawing head comprises curved recess (5) in the bent section of the jawing head; i.e. an opening in the bending section of the closed jawing head.
2. The surgical forceps according to embodiment 1, wherein the jaws comprise an outward bend in the bended section of the jawing head, thus creating an opening with outward bent jawing heads in the bending section of the closed jawing head. As explained above, having an opening in the bent section of the jawing head, more in particular with outward bent jaws, the forceps of the invention has an opening to enclose a gulp of neuropathic skin. Skin neuropathies like hard calluses are not restricted to the upper surface of the skin but penetrate deeper in the skin tissue. By creating the possibility of enclosing a skin area, the accessibility to the underlying skin deficiency is enhanced, allowing a much better treatment of deeper skin neuropathies like hard calluses.

3. The surgical forceps according to embodiment 2 wherein the curved recess, i.e. the opening in the bending section of the closed jawing head is an ovally shaped recess.
4. The surgical forceps according to any one of embodiments 1 to 3 wherein the curved recess is bent under an angle between 90° and 130°; in particular between 110° and 120°; more in particular about 120°, such as 116°, 117°, 118°, 119°, 120°, 121°, 122°, 123° and 124°; in particular the bend in the jawing head is between 90° and 130°.
5. The surgical forceps according to any one of the foregoing embodiments wherein the curved recess is configured as a V-shaped groove. Positioning in the bend, in particular having an angle between 90° and 130°, and even more in particular V-Shaped, allows the forceps, when positioned around the neuropathic skin to be pushed and exert a downward pressure to the surrounding tissue which is compensated by an upward movement of the tissue enclosed by the jaws. It accordingly contributes in the accessibility to the underlying skin deficiency, allowing a much better treatment of deeper skin neuropathies like hard calluses.
6. The surgical forceps according to any one of the foregoing embodiments wherein the curved recess comprises tapered jaws (11) at the inside of the curved recess. Such tapered jaws enhance the aforementioned upward push of the enclosed gulp of neuropathic skin making it easier accessible for decallusing. As mentioned below, these tapered jaws could optionally comprise a series of clamping teeth (8) further enhancing the grip on the enclosed gulp of neuropathic skin.
7. In one embodiment the surgical forceps according to the invention is further characterized in that the jaws are thickened and slightly rounded, when compared to the jaws typically seen in a mosquito forceps, or when compared to the tip of the jaw head.
8. As explained below, it could be beneficial within the purpose of wound treatment that the non-bent part of the jaws is extended. Thus in one embodiment of the surgical forceps according to the invention the non-bent part of the jaws is extended.
9. As already mentioned herein before, in one embodiment of the surgical forceps according to the invention the jawing head, including the curved recess is provided with a series of clamping teeth (8); in particular closely spaced clamping teeth at the inside of the jaws.
10. As further detailed below, in the application of wound healing also certain adaptations to the handle shanks (2) could be beneficial for the ergonomics of the user and the strength of the device. These include that the handle shanks comprise one or more of the following features, i.e. that the handle shanks are slightly bent; that the handle shanks are extended; and in that the handle shanks are thickened with the thickening being the largest at the pivoting point (4) and progressively reducing towards the handles. In particular comprising all of said features.
11. In a further embodiment the surgical forceps according to the invention is characterized in that the pivoting point is thickened when compared to the rest of the forceps.
12. In a further embodiment the surgical forceps according to the invention is characterized comprising a locking grip (3); in particular the locking grip having 3-5 teeth.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

As mentioned herein before, the grabbing functionality of the current mosquito forceps is limited. This results in poor stability of the tool and as a consequence bad handling control.

In order to solve the 'problem' an additional curved recess (5) on the forcep's jawing head is added to the prior art Mosquito forceps. More specifically, the curved recess is positioned in the bent section of the jawing head. The idea is to use the curved recess, i.e. the opening in the closed jawing head, as another neuropathic skin grabbing functionality option. Grabbing the neurophatic skin with the curved recess solves the 'problem' in the sense that: i) due to the fact that the grabbing surface is significantly larger a skin bulb can be grabbed, the total force and grip level can be significantly increased; ii) the force distribution is equally distributed over a larger contact surface of the skin, thus signficantly decreasing the risk of causing additional skin damage; iii) the new position of the grabbing item (infra), in addition with the ability to grap a bulb of the skin, decreases the level of degree of freedom of the forceps, and thus allowing for a significantly increased handling stability.

Figure 1:
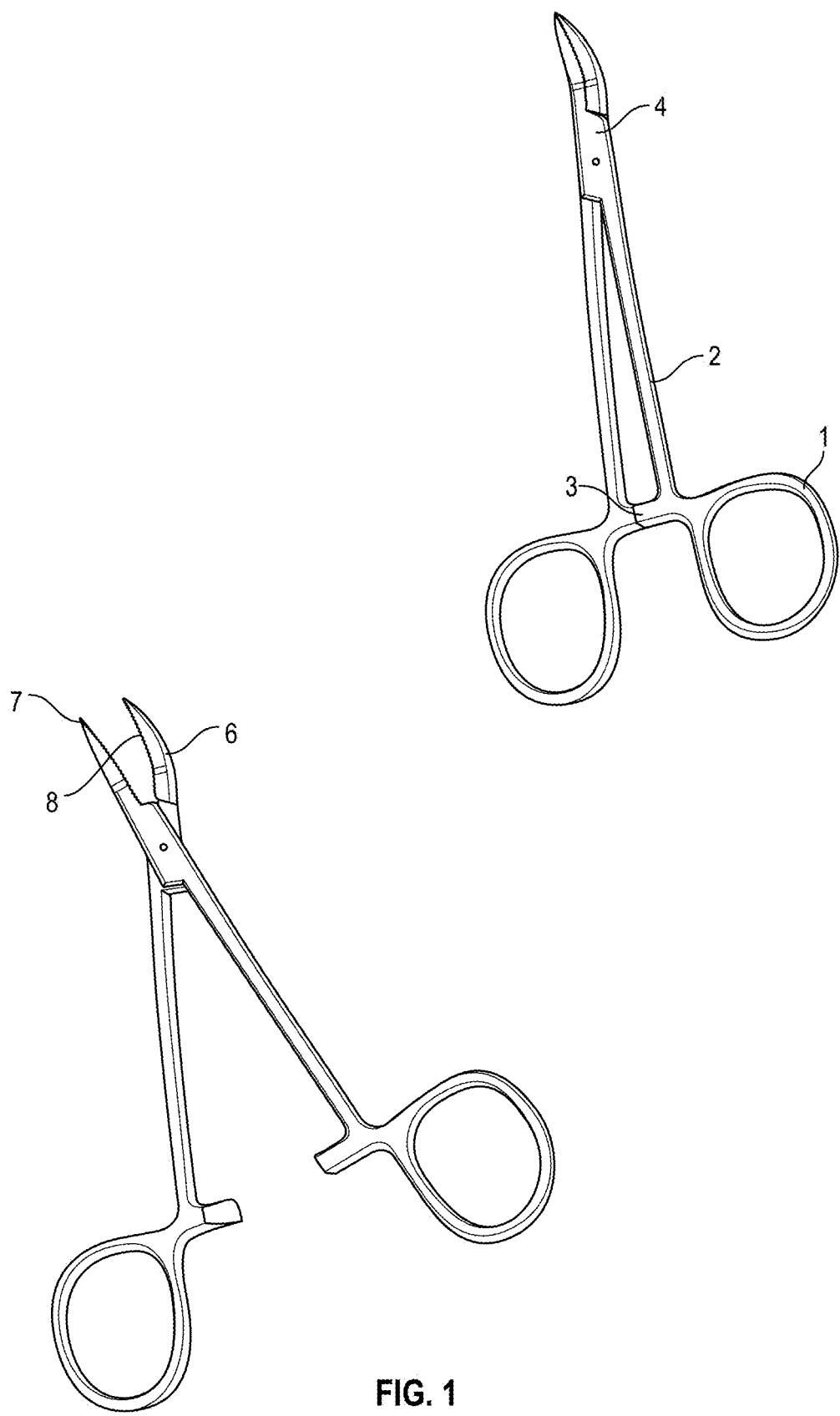
FIG. 1: Technical drawing of an original Mosquito Forceps: Closed and open position—Showing the pair of handle rings (1); the handle shanks (2); the locking grip (tongues/catch) (3); the pivotal connection (4); the jaws making up the jawing head (6). In this example the jaws are bent and end in a sharp tip (7) and are provided at the inside with a series of clamping teeth (8).
Figure 2:
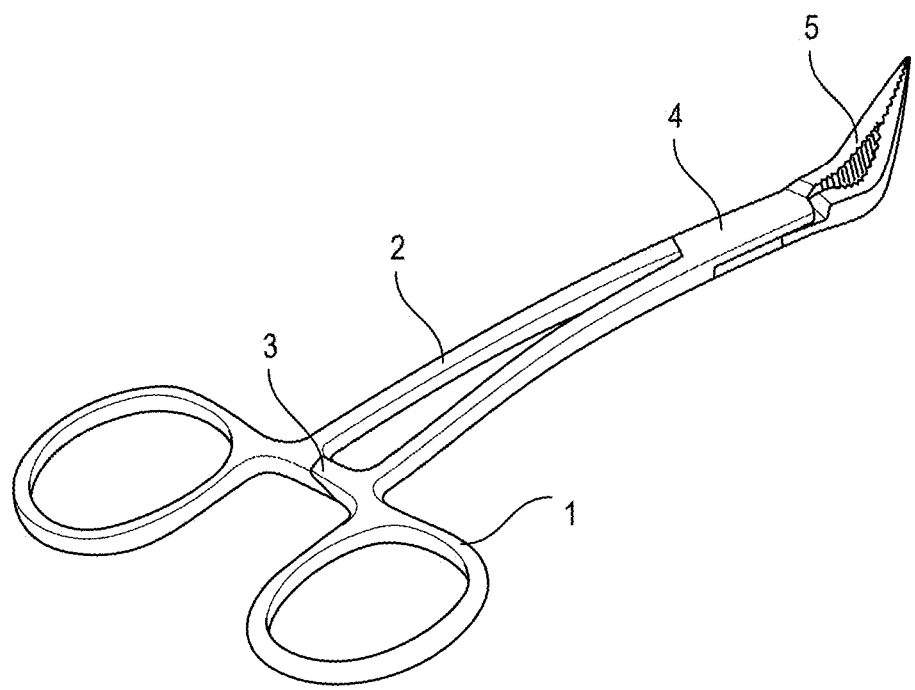
FIG. 2: Technical drawing of a Forceps according to the invention: Closed and open position—Showing the common features of the Mosquito Forceps; i.e. the pair of handle rings (1); the handle shanks (2); the locking grip (tongues/catch) (3); the pivotal connection (4); the jaws making up the jawing head; but differing in the jaws comprising an outward bend in the curved part of the jaws. Together they create a curved recess (5) In the jawing head.
Figure 2:
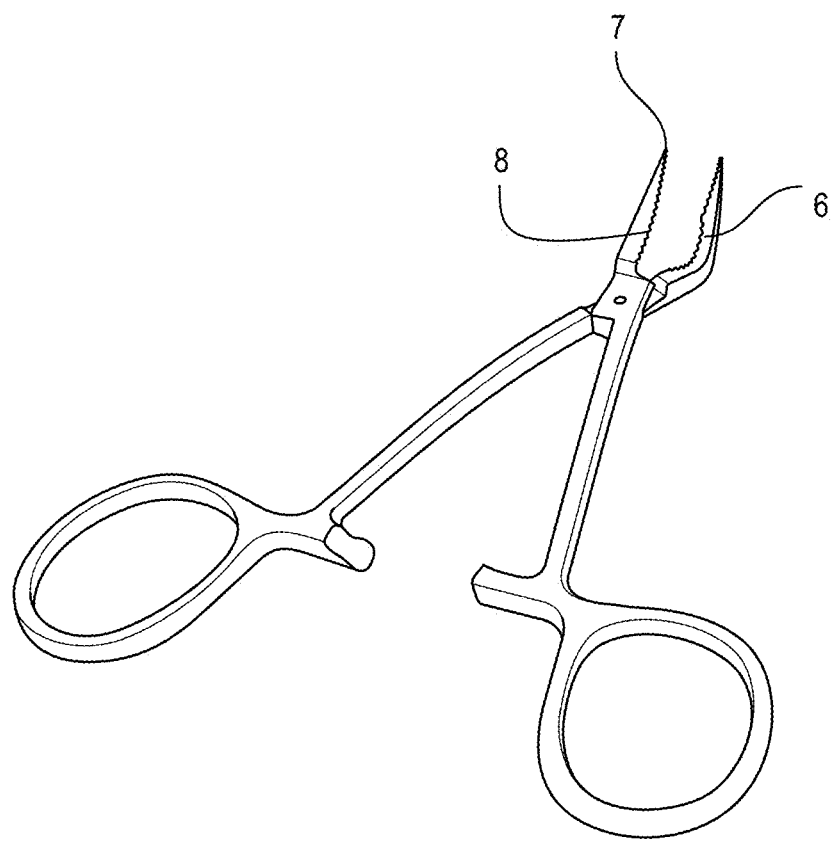

Per reference to FIGS. 1 and 2, most of the design and technical specifications are identical to the original tooling. The forceps consists of a pair of handle rings (1), with one ring on each side member. It is connected to the pair of prolonged handle shanks (2), which are pivoted (4) together and manipulate the jawing head (6). In a preferred embodiment the shanks are slightly bent as such to provide improved handling ergonomics. A pivoting point (4) connects the handling shanks to the jawing head. The jawing head incorporates the newly invented curved recess (5), which provides the primary neurophatic skin grabbing functionality. In one embodiment it is an ovally spaced recess, allowing for effective grabbing, locking and manipulating of a skin bulb. The jaws still end in a sharp jawing head tip (7) similar to the tip in the prior art mousquito forceps and still provides the original grabbing and pinching functionality. It is sharp and pointy, in order to be able to provide the adequate pinching force and it is largely bent in targetting the appropriate ergonomics. In one embodiment the jawing head and the newly invented curved recess (5) is provided with a series of clamping teeth (8) to provide the adequate gripping level. In the example shown in FIG. 3 the clamping teeth are closely spaced. A locking tongue or catch, herein also referred to as a locking grip (3) is provided in order to fix/lock the handles shanks together. In one embodiment the locking grip has 3-5 teeth to allow ratchet clamping at various pressures.

Figure 3:
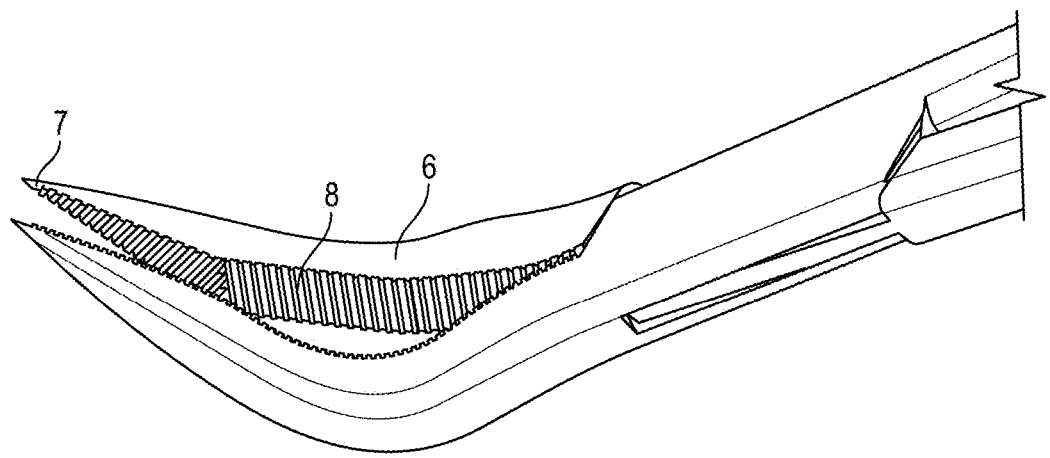
FIG. 3: Zoomed view of the jawing head of a forceps according to the invention. In this shown embodiment also the outwardly bent part in the curved part of the jaws comprises clamping teeth (8) at the inside of the jaws.

Per reference to FIG. 3, in positioning the curved recess (5) in the jawing head it was found that it is best built in at the bending position of the jaws in the jawing head and characterized in an outward bent of the jaws at said position (infra). The angle of the curved recess is typically between 90° and 130°; in particular between 110° and 120°; more in particular about 120°, such as 116°, 117°, 118°, 119°, 120°, 121°, 122°, 123° and 124°. In a particular embodiment the curved recess is configured as a V-shaped groove, more in particular a V-shaped groove wherein the angle of said V-shaped groove is between 90° and 130°; in particular between 110° and 120°; more in particular about 120°, such as 116°, 117°, 118°, 119°, 120°, 121°, 122°, 123° and 124°. Compared to the prior art mosquito forceps the non-bent part of the jaws could be extended in order to provide more space for the curved recess, but elongation of the jawing shanks not only provides more space for the curved recess it also adds improved ergonomics to the tool and creates a larger momentum on the grabbed material. This allows the therapist to better control and to exert a larger force in handling the grabbed material. The foregoing effects could be further enhanced by an extension of the handling shanks (2) when compared to a prior art mosquito forceps.

The bend in the jaws in the jawing head is typically between 90° and 150°; in particular between 110° and 130°; more in particular about 130°. In one embodiment the jawing head is thickened and slightly rounded when compared to a prior art mosquito forceps. Such thickened jawing head reduces the inner stress on the jawing beams when applying force. This is particularly suitable in said embodiments wherein the non-bent part of the jaws are extended and/or the handling shanks are extended. In said embodiment wherein the handling shanks are extended, and the non-bent part of the jaws are extended, higher handling forces can be exerted. In order to comply with the increased moment on such elongated handle shanks, without effecting inner stresses, the handles shanks could be thickened. In the idea of logic design and reduction of raw materials usage, in one such embodiment the thickening is the largest at the pivoting point and reduces progressively towards the handles. Alternatively, only the pivoting point could be thickened to comply with the increased moment on the handles shanks.

Figure 4:
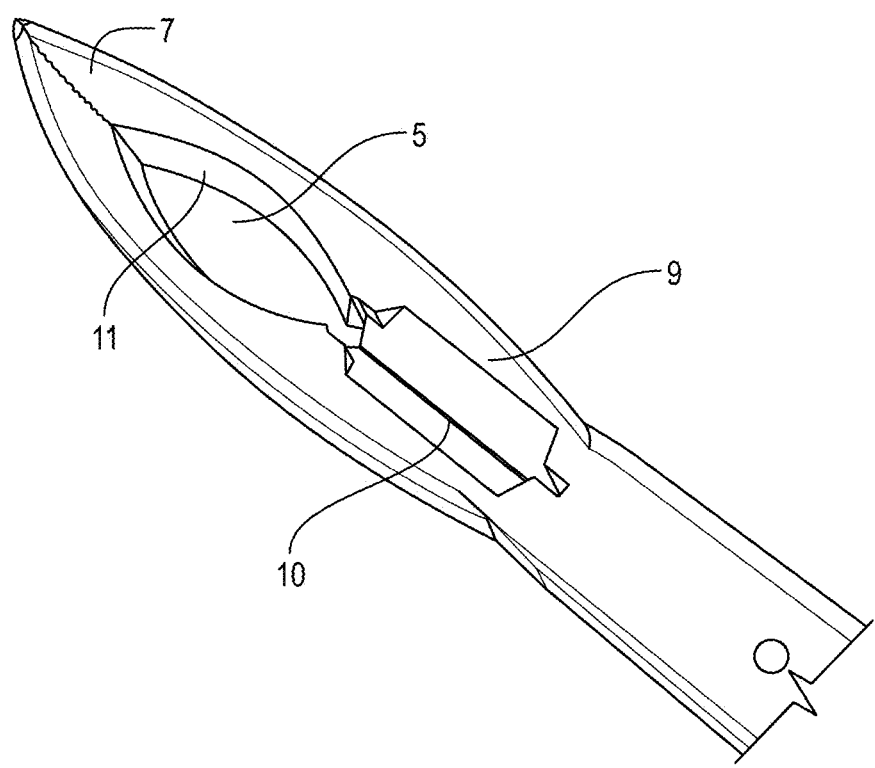
FIG. 4: Zoomed view of the jawing head of a forceps according to the invention. In this shown embodiment the outwardly bent part in the curved part of the jaws comprises tapered jaws (11) at the inside of the jaws, and the jaws head further comprises a cutting area (10).

In FIG. 4 another embodiment is shown adding a cutting area (9) to the tool. In this embodiment all actions needed debridement of skin wounds, can be performed with a single tool. Picking of dirt or small isolated dead tissue particles by means of the sharp tips (7), decallusing through the bent recess (5) to enclose the neuropathic skin, and excision or clipping of loose or loosened material from the wound by means of the cutting area (9).

These and other embodiments will be apparent for the skilled person from the claims hereinafter.

The parts list of the forceps consist of the following:
1) The pair of handle rings
2) Handles shanks
3) Locking tongues/catch
4) Pivotal connection
5) Curved recess (Invention)
6) Jawing head
7) Bent tip
8) Series of clamping teeth
9) Cutting Area
10) Cutting Edge
11) Tapered Jaw parts

The invention claimed is:
1. A surgical forceps configured for grabbing a skin bulb for neuropathic wound debridement, the surgical forceps comprising:
a pair of handle shanks comprising:
a pair of handling rings at a first end;
and a pair of jaws making up a jawing head at a second end opposite the first end, wherein:
the jawing head has an open position and a closed position;
the pair of jaws is pivotably connected by a pivotal connection to the pair of handling rings to pivot the pair of jaws between the open position and the closed position by opening or closing the pair of handling rings in a direction essentially perpendicular with the pair of handle shanks;
each jaw comprises: a non-bent section connected to a respective handling ring and oriented in a direction essentially parallel and in plane with the pair of handle shanks;
and a bent section connected to the non-bent section such that the bent section forms a bent tip oriented in a direction essentially parallel and out of plane with the pair of handle shanks;
the non-bent section and the bent section of each jaw defines a curved recess on an inner side of each jaw,—such that an opening is defined by the jawing head when the jawing head is in the closed position;
the inner sides of the jaws comprise a series of clamping teeth;
the bent sections of the jaws comprise an outward bend on an outer side of each jaw;

the outward bends extend outwardly as viewed in the direction essentially parallel with the pair of handle shanks;

and the pair of jaws increase a total force and grip level on the skin bulb, by gripping the skin bulb between the clamping teeth, when the jawing head is in the closed position over the skin bulb during the neuropathic wound debridement.

2. The surgical forceps of claim 1, wherein the opening is an oval-shaped opening.

3. The surgical forceps of claim 1, wherein the curved recesses are bent under an angle between 90° and 130°.

4. The surgical forceps of claim 1, wherein the curved recesses are configured as V-shaped grooves.

5. The surgical forceps of claim 1, wherein the outward bends of the bent sections in the jawing head are between 90° and 130°.

6. The surgical forceps of claim 1, wherein the jaws are thickened and slightly rounded.

7. The surgical forceps of claim 1, wherein the non-bent sections of the jaws are extended from the bent sections of the jaws in a longitudinal direction.

8. The surgical forceps of claim 1, wherein the handle shanks are slightly bent.

9. The surgical forceps of claim 1, wherein the handle shanks are extended in a longitudinal direction of the surgical forceps.

10. The surgical forceps of claim 1, wherein the handle shanks are thickened, with the thickening being the largest at the pivoting point and progressively reducing toward the handles.

11. The surgical forceps of claim 1, wherein pivoting point is thickened when compared to the rest of the forceps.

12. The surgical forceps of claim 1, further comprising a locking grip.

13. The surgical forceps of claim 12, wherein the locking grip has 3 to 5 teeth.

* * * * *